United States Patent [19]

Tsuda et al.

[11] Patent Number: 4,871,766

[45] Date of Patent: Oct. 3, 1989

[54] OIL-IN-WATER PESTICIDAL EMULSION

[75] Inventors: Shigenori Tsuda, Kyoto; Yukio Manabe, Toyonaka; Kozo Tsuji, Nara, all of Japan

[73] Assignee: Sumitomo Chemical Company, Limited, Osaka, Japan

[21] Appl. No.: 947,271

[22] Filed: Dec. 29, 1986

[30] Foreign Application Priority Data

Jan. 17, 1986 [JP] Japan .................................. 61-8455

[51] Int. Cl.$^4$ .................... A01N 31/14; A01N 37/34; A01N 53/00; A01N 57/00
[52] U.S. Cl. ............................... 514/521; 514/89; 514/345; 514/421; 514/479; 514/490; 514/531; 514/721; 514/938
[58] Field of Search ............... 514/938, 521, 531, 89

[56] References Cited

U.S. PATENT DOCUMENTS

Re. 31,927  6/1985  Coffee et al. ..................... 514/521
4,737,520  4/1988  Naik et al. ........................ 514/520

FOREIGN PATENT DOCUMENTS 0000962  3/1979  European Pat. Off. ............ 514/321
2048675  12/1980  United Kingdom ................ 514/531

*Primary Examiner*—Allen J. Robinson
*Attorney, Agent, or Firm*—Stevens, Davis, Miller & Mosher

[57] ABSTRACT

An oil-in-water pesticidal emulsion which comprises one or more of hydrocarbons represented by the formula,

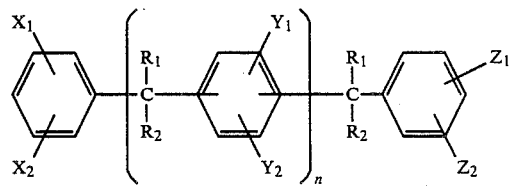

wherein $X_1$, $X_2$, $Y_1$, $Y_2$, $Z_1$ and $Z_2$, which may be the same or different, represent a hydrogen atom or an alkyl group having two or less carbon atoms, $R_1$ and $R_2$, which may be the same or different, represent a hydrogen atom or a methyl group, and n represents 0 or 1, in an oil-in-water pesticidal emulsion containing an active ingredient having a pesticidal activity, of which the melting point is 0° C. or higher and the solubility at 0° C. in the hydrocarbons represented by the above formula is 10 wt. % or more (when two or more active ingredients are used together, said melting point and solubility shall be those of a mixture of these active ingredients).

4 Claims, No Drawings

OIL-IN-WATER PESTICIDAL EMULSION

The present invention relates to an oil-in-water pesticidal emulsion which comprises one or more of hydrocarbons represented by the formula (I),

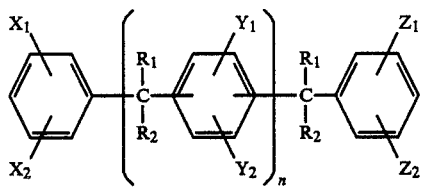

wherein $X_1$, $X_2$, $Y_1$, $Y_2$, $Z_1$ and $Z_2$, which may be the same or different, represent a hydrogen atom or an alkyl group having two or less carbon atoms, $R_1$ and $R_2$, which may be the same or different, represent a hydrogen atom or a methyl group, and n represents 0 or 1, in an oil-in-water pesticidal emulsion containing an active ingredient having a pesticidal activity, of which the melting point is 0° C. or higher and the solubility at 0° C. in the hydrocarbons represented by the above formula (I) is 10 wt. % or more (when two or more active ingredients are used together, said melting point and solubility shall be those of a mixture of these active ingredients) and its production and use.

According to the present invention, pesticidal oil-in-water emulsion formulations which are very stable even after prolonged storage can be obtained. The pesticidal oil-in-water emulsion formulations of the present invention can be used as ones which are safe to users, cause little phytotoxicity, and besides which are superior in storage stability.

Among the conventional pesticidal formulations which are applied by liquid spraying, emulsifiable concentrates, which are generally formulated with active ingredients, synthetic surfactants and large quantities of organic solvents, have frequently defects owing to the organic solvents such as inflammability, offensive odor, toxicity and irritation effect to mammals, phytotoxicity to crops, etc.

On the other hand, there are wettable powders as a powder type formulations containing no organic solvents. It cannot be denied, however, that these wettable powders also have defects: In preparing the spray liquid, very fine powders may be inhaled by an operator, so that handling is inconvenient; and low-volume space spraying of high-concentration spray liquid is diffucult.

For this reason, there have been studied the so-called flowable formulations in which hydrophobic active ingredients have been suspended and dispersed in fine particles in water used as a base in place of organic solvents and powdery carriers. This kind of formulation can be handled like the conventional liquid formulations and there is no scattering of fine powders during the preparation of spray liquid unlike wettable powders. Besides, this kind of formulation uses water as a base unlike emulsifiable concentrates containing organic solvents as a base, so that there are few problems owing to organic solvents such as toxicity and irritation effect to mammals as well as phytotoxicity to crops.

Various kinds of technique have been already well known about the preparation of pesticidal flowable formulations. These well-known techniques are roughly divided into two: One is a method in which a solid toxicant is pulverized into fine particles which are then suspended in water, and the other is a method in which a liquid toxicant is emulsified in fine particles in water using a dispersing agent to obtain an aqueous emulsion. The former is disclosed in Japanese Patent Publication No. 46,889/1978, and the latter is disclosed in Japanese Patent Application Kokai (Laid-open) No. 124,707/1980.

In the former technique, fine particles of a solid toxicant are suspended in water, but when these fine particles are stored in water over a long period of time, the followings were found frequently: They gradually dissolve in water and, depending upon the variation of storage temperature, deposit as crystals on the suspended particles, as a result of which the suspended particles increase in size to fail to keep the suspended state.

In the latter technique, a liquid toxicant is generally used, but when the melting point of the toxicant is in the vicinity of room temperature, the followings were sometimes found: If the toxicant in the emulsion is present as a liquid immediately after preparation of the formulation, it crystallizes when stored at a low temperature over a long period of time to affect the suspended state.

In spite of these problems, however, these defects have been covered up to some degree by selecting proper dispersing agents and thickening agents, and thus formulations which are not satisfactory but fit for practical use have been produced.

An object of the present invention is to attain the perfect prevention of growth of crystals or crystallization which could not be attained by the conventional techniques. For this purpose, it is most important to completely liquefy the active ingredient to prevent the crystallization thereof, and for liquefying the active ingredient, addition of solvents is necessary. However, in order that the solvents can be added to the flowable formulations, it is required for the solvents not to do a great damage to various advantages peculiar to the formulations such as low inflammability, low toxicity to mammals, low phytotoxicity, etc. Also, for liquefying the active ingredient, the solvents should have good solubility for the active ingredient. Further, the solvents need to be insoluble in water and besides to hold the active ingredient even after dispersed in water.

As described above, various problems are concerned in the selection of solvents, although it is easy to say that the active ingredient is liquefied by means of solvents.

The present inventors extensively studied for a long time to solve these problems, and as a result, succeeded in obtaining stabilized pesticidal flowable formulations using solvents of few problems. The present inventors thus completed the present invention.

That is, the present inventors succeeded in solving the foregoing problems peculiar to the pesticidal flowable formulations by mixing an active ingredient with one or more of hydrocarbons represented by the foregoing formula (I) into a uniform solution which is then formulated into pesticidal flowable formulations. Referring now to this method in detail, stabilized pesticidal flowable formulations which are free from growth of crystals and crystallization can be obtained by uniformly dissolving an active ingredient having a pesticidal activity, of which the melting point is 0° C. or higher and the solubility at 0° C. in the hydrocarbons represented by the above formula (I) is 10 wt. % or more (when two or more active ingredients are used together, said melting point and solubility shall be those of a mixture of these ingredients) in one or more of said hydrocarbons, emulsifying and suspending the resulting solution in water using a dispersing agent and if necessary, adding other additives such as thickening agent, etc.

When the active ingredient and the hydrocarbons represented by the above formula (I) are separately emulsified and suspended in water using a dispersing agent, the particles of the active ingredient and those of the hydrocarbon are present independently in the resulting pesticidal flowable formulation. Consequently, the effect to prevent growth of crystals and crystallization, which is not developed until the both particles are combined to form a uniform solution, becomes to fail to appear.

In order to obtain the stabilized pesticidal flowable formulations of the present invention which are free from growth of crystals and crystallization, it is therefore necessary to first dissolve the active ingredient in said hydrocarbon and disperse the resulting solution in water.

According to the present invention, the longterm storage stability of flowable formulations containing active ingredients having a melting point of 0° C. or higher can be improved, and also there is no adverse effect on the activity by the addition of the solvent. In addition, there is no great damage to various advantages peculiar to the formulations such as low inflammability, low toxicity to mammals, low phytotoxicity, etc. Also, even active ingredients which could never be formulated into flowable formulations by the conventional techniques, for example those which are highly soluble in water and show a remarkable crystal growth during storage in water, can easily be formulated into flowable formulations by using the technique of the present invention.

The active ingredient having a pesticidal activity referred to herein includes for example pyrethroid compounds, carbamate compounds, organo-phosphate compounds, etc. More specifically, there may be mentioned compounds as shown in Table 1.

TABLE 1

| Active ingredient | Name of compound |
|---|---|
| (a) | 2-Sec-butylphenyl N—methylcarbamate |
| (b) | α-Cyano-3-phenoxybenzyl 3-(2,2-dichlorovinyl)-2,2-dimethylcyclopropanecarboxylate |
| (c) | O—(3,5,6-Trichloro-2-pyridyl) O,O—diethylphosphorothioate |
| (d) | 3-Phenoxybenzyl 3-(2,2-dichlorovinyl)-2,2-dimethylcyclopropanecarboxylate |
| (e) | α-Cyano-3-phenoxybenzyl 2,2,3,3-tetramethylcyclopropanecarboxylate |
| (f) | α-Cyano-3-phenoxybenzyl 2-(4-chlorophenyl)-3-methylbutyrate |
| (g) | 3,4,5,6-Tetrahydrophthalimidemethyl chrysanthemate |
| (h) | 2-{1-Methyl-2-(4-phenoxyphenoxy)ethoxy} pyridine |
| (i) | 3-Phenoxybenzyl 2-(4-ethoxyphenyl)-2-methylpropyl ether |

The hydrocarbon represented by the formula (I) includes the following compounds shown in Table 2.

TABLE 2

| Hydrocarbon | Name of Compound |
|---|---|
| (1) | 1,1-Diphenylethane |
| (2) | 1,1-Ditolylethane |

TABLE 2-continued

| Hydrocarbon | Name of Compound |
|---|---|
| (3) | 1-Phenyl-1-xylylethane |
| (4) | 1-Phenyl-1-(ethylphenyl)ethane |
| (5) | 1-Xylyl-1-(α-methylbenzylphenyl)-ethane |
| (6) | Bis-(α-methylbenzyl)xylene |

Both the active ingredient and the hydrocarbon sometimes have isomers, in which case these isomers are of course included in the scope of the present invention. These active ingredients and hydrocarbons may be used in combination, respectively.

The dispersing agent includes for example polyvinyl alcohol, gum arabic, etc. The thickening agent includes for example water-soluble polymeric thickening agents (e.g. polyacrylic acid type thickening agents, thickening agents belonging to natural polysaccharides), inorganic thickening agents, etc.

A step wherein the oily phase containing the active ingredient and the hydrocarbon is emulsified in the aqueous phase using a dispersing agent, will be explained below. When the step is carried out in a batch system, it is preferred to limit the amount of the oily phase to be dispersed to 3 parts by weight or less based on 1 part by weight of the aqueous phase. When the step is carried out in a continuous system, it is preferred to adjust the amounts per unit time of the oily and aqueous phases to be sent to a dispersing apparatus so that the amount of the former is 3 parts by weight or less based on 1 part by weight of the latter.

The amount of the hydrocarbon added is generally from 0.1 to 10 parts by weight based on 1 part by weight of the active ingredient.

Also, either of the proportions of the dispersing and thickening agents in the formulations is from 0.1 to 20 wt. %.

The oil-in-water emulsion formulations of the present invention can be applied as pesticides, such as insecticides, acaricides, nematocides, herbicides, plant growth regulators, etc. for use in agriculture and horticulture, exterminating agents for pests causing epidemics such as mosquitoes, flies, cockroaches, termites, etc., and exterminating agents for pests (e.g. mites, flies, gadflies, fleas, lice) parasitic on cattle, sheep, pigs, domestic animals (e.g. fowls, dogs, cats), etc.

The present invention will be illustrated in more detail with reference to the following examples, comparative examples and test examples.

EXAMPLE 1

The active ingredient (f) is a viscous liquid at room temperature and solidifies at 0° C. Its solubility in the hydrocarbon (3) is 50 wt. % or more at 0° C.

A mixture of 10 g of the active ingredient (f) and 10 g of the hydrocarbon (3) was well mixed to completely dissolve the former in the latter. This solution was added to 30 g of a 13.3 wt. % aqueous solution of Gosenol GL-05 ® (polyvinyl alcohol) a trade name of Nippon Gosei Kagaku Kogyo Co.; polymerization degree, 1000 or less; saponification degree, 86.5–89.0%), and the mixed solution was stirred at 70° C. for 5 minutes at a rate of 7000 rpm by means of T.K. Homomixer ® (a trade name of Tokushu Kika Kogyo Co.). Thereafter, 50 g of an aqueous solution containing 0.4 wt. % of Kelzan S ® (xanthane gum, a trade name of Kelco Co., U.S.A.) and 0.8 wt. % of Veegum ® (aluminum magnesium silicate; a trade name of Vanderbilt Co., U.S.A.) was added at room temperature and mixed for several minutes with mild stirring to obtain 100 g of an oil-in-water emulsion formulation containing 10 wt. % of the active ingredient.

Example 2

The active ingredient (e) is a viscous liquid at room temperature and solidifies at 0° C. Its solubility in the hydrocarbon (3) is 50 wt. % or more at 0° C.

A mixture of 2.5 g of the active ingredient (e) and 2.5 g of the hydrocarbon (3) was well mixed to completely dissolve the former in the latter. This solution was added to 40 g of a 10 wt. % aqueous solution of Gosenol GL-05 ® (the same as above), and the mixed solution was stirred at 70° C. for 5 minutes at a rate of 7000 rpm by means of T.K. Homomixer ® (the same as above). Thereafter, 55 g of an aqueous solution containing 20 wt. % of Agrisol FL 100F ® (polyacrylic acid type thickening agent; a trade name of Kao Co.) previously neutralized was added at room temperature and mixed for several minutes with mild stirring to obtain 100 g of an oil-in-water emulsion formulation containing 2.5 wt. % of the active ingredient.

Example 3

The active ingredient (b) is a viscous liquid at room temperature, but crystallizes in part when stored at 0° C. for a long time. Its solubility in the hydrocarbon (2) is 50 wt. % or more at 0° C.

A mixture of 6 g of the active ingredient (b) and 6 g of the hydrocarbon (2) was well mixed to completely dissolve the former in the latter. This solution was added to 40 g of a 10 wt. % aqueous gum arabic solution, and the mixed solution was stirred at 70° C. for 5 minutes at a rate of 7000 rpm by means of T.K. Homomixer ® (the same as above). Thereafter, 48 g of an aqueous solution containing 0.5 wt. % of Kelzan S ® (the same as above) and 1.0 wt. % of Veegum ® (the same as above) was added at room temperature and mixed for several minutes with mild stirring to obtain 100 g of an oil-in-water emulsion formulation containing 6 wt. % of the active ingredient.

EXAMPLE 4

The active ingredient (d) is a viscous liquid at room temperature and solidifies at 0° C. Its solubility in the hydrocarbon (4) is 50 wt. % or more at 0° C.

A mixture of 10 g of the active ingredient (d) and 10 g of the hydrocarbon (4) was well mixed to completely dissolve the former in the latter. This solution was added to 40 g of a 10 wt. % aqueous solution of Gosenol GL-05 ® (the same as above), and the mixed solution was stirred at 70° C. for 5 minutes at a rate of 7000 rpm by means of T.K. Homomixer ® (the same as above). Thereafter, 40 g of an aqueous solution containing 0.5 wt. % of Kelzan S ® (the same as above) and 1.0 wt. % of Veegum ® (the same as above) was added at room temperature and mixed for several minutes with mild stirring to obtain 100 g of an oil-in-water emulsion formulation containing 10 wt. % of the active ingredient.

EXAMPLE 5

The active ingredient (h) is a solid at room temperature. Its solubility i the hydrocarbon (6) is 10 wt. % at 0° C.

A mixture of 1 g of the active ingrednet (h) and 9 g of the hydrocarbon (6) was well mixed to completely dissolve the former in the latter. This solution was added to 40 g of a 10 wt. % aqueous gum arabic solution, and the mixed solution was stirred at 70° C. for 5 minutes at a rate of 7000 rpm by means of T.K. Homomixer ® (the same as above). Thereafter, 50 g of a 20 wt. % aqueous solution of Agrisol FL 100F ® (the same as above) previously neutralized was added at room temperature and mixed for several minutes with mild stirring to obtain 100 g of an oil-in-water emulsion formulation containing 1 wt. % of the active ingredient.

EXAMPLE 6

The active ingredient (a) is a semi-solid at room temperature and solidifies at 0° C. Its solubility in the hydrocarbon (5) is 50 wt. % or more at 0° C.

A mixture of 10 g of the active ingredient (a) and 10 g of the hydrocarbon (5) was well mixed to completely dissolve the former in the latter. This solution was added to 30 g of a 13.3 wt. % aqueous solution of Gosenol GL-05 ® (the same as above), and the mixed solution was stirred at 70° C. for 5 minutes at a rate of 7000 rpm by means of T.K. Homomixer ® (the same as above). Thereafter, 50 g of a 20 wt. % aqueous solution of Agrisol FL104FA ® (a thickening agent belonging to saccharide derivatives; a trade name of Kao Co.) was added and mixed for several minutes with mild stirring to obtain 100 g of an oil-in-water emulsion formulation containing 10 wt. % of the active ingredient.

EXAMPLE 7

Both the active ingredients (c) and (g) are a solid at room temperature, and a mixture of them is also a solid. The solubility of a 10 : 1 (by weight) mixture of the active ingredients (c) and (g) in a 2 : 8 (by weight) mixture of the hydrocarbons (1) and (3) is 25 wt. % or more at 0° C.

To a mixture of 5 g of the active ingredient (c) and 0.5 g of the active ingredient (g) was added 16.5 g of a 2 : 8 (by weight) mixture of the hydrocarbons (1) and (3), and the resulting mixture was well mixed to completely dissolve the former in the latter. This solution was added to 40 g of a 10 wt. % aqueous solution of Gosenol GL-05 ® (the same as above), and the mixed solution was stirred at 70° C. for 5 minutes at a rate of 7000 rpm by means of T.K. Homomixer ® (the same as above). Thereafter, 40 g of an aqueous solution containing 0.5 wt. % of Kelzan S ® (the same as above) and 1.0 wt. % of Veegum ® (the same as above) was added and mixed for several minutes with mild stirring to obtain 100 g of an oil-in-water emulsion formulation containing 10 wt. % of the active ingredients.

EXAMPLE 8

A mixture of 15 g of the active ingredient (f) and 45 g of the hydrocarbon (3) was well mixed to completely dissolve the former in the latter. This solution was added to 440 g of a 10 wt. % aqueous solution of Gosenol GL-05 ® (the same as above), and the mixed solution was stirred at room temperature for 10 minutes at a rate of 500 rpm by means of T.K. Homomixer ® (the same as above). Thereafter, 500 g of an aqueous solution containing 0.4 wt. % of Kelzan S ® (the same as above) and 1.2 wt. % of Veegum (the same as above) was added at room temperature and mixed for several minutes with mild stirring to obtain 1000 g of an oil-in-water emulsion formulation containing 1.5 wt. % of the active ingredient.

EXAMPLE 9

A mixture of 100 g of the active ingredient (f) and 200 g of the hydrocarbon (3) was well mixed to completely dissolve the former in the latter. This solution was added to 400 g of a 15 wt. % aqueous solution of Gosenol GL-05 ® (the same as above), and the mixed solution was stirred at 40° C. for 5 minutes at a rate of 8000 rpm by means of T.K. Homomixer ® (the same as above). Thereafter, 300 g of an aqueous solution containing 0.6 wt. % of Kelzan S ® (the same as above) and 1.0 wt. % of Veegum ® (the same as above) was added at 40° C and mixed for several minutes with mild stirring to obtain 1000 g of an oil-in-water emulsion formulation containing 10 wt. % of the active ingredient.

EXAMPLE 10

A mixture of 50 g of the active ingredient (f) and 100 g of the hydrocarbon (3) was well mixed to completely dissolve the former in the latter. This solution was added to 400 g of a 15 wt. % aqueous solution of Gosenol GL-05 ® (the same as above), and the mixed solution was stirred at 55° C. for 5 minutes at a rate of 7500 rpm by means of T.K. Homomixer ® (the same as above). Thereafter, 450 g of a 0.6 wt. % aqueous solution of Kelzan S ® (the same as above) was added at room temperature and mixed for several minutes with mild stirring to obtain 1000 g of an oil-in-water emulsion formulation containing 5 wt. % of the active ingredient.

COMPARATIVE EXAMPLE 1

Ten grams of the active ingredient (f) was heated to 70° C. to obtain a completely liquefied solution. This solution was added to 30 g of a 13.3 wt. % aqueous solution of Gosenol GL-05 ® (the same as above), and the mixed solution was stirred at 70° C. for 5 minutes at a rate of 0 7000 rpm by means of T.K. Homomixer ® (the same as above). Thereafter, 60 g of an aqueous solution containing 0.48 wt. % of Kelzan S ® (the same as above) and 0.96 wt. % of Veegum ® (the same as above) was added at room temperature and mixed for several minutes with mild stirring to obtain 100 g of a flowable formulation containing 10 wt. % of the active ingredient.

COMPARATIVE EXAMPLE 2

2.5 Grams of the active ingredient (e) was heated to 70° C. to obtain a completely liquefied solution. This solution was added to 40 g of a 10 wt. % aqueous solution of Gosenol GL-05 ® (the same as above), and the mixed solution was stirred at 70° C. for 5 minutes at a rate of 7000 rpm by means of T.K. Homomixer ® (the same as above). Thereafter, 57.5 g of a 20 wt. % aqueous solution of Agrisol FL 100F ® (the same as above) previously neutralized was added at room temperature and mixed for several minutes with mild stirring to obtain 100 g of a flowable formulation containing 2.5 wt. % of the active ingredient.

COMPARATIVE EXAMPLE 3

Ten grams of the active ingredient (d) was heated to 70° C. to obtain a completely liquefied solution. This solution was added to 40 g of a 10 wt. % aqueous solution of Gosenol GL-05 ® (the same as above), and the mixed solution was stirred at 70° C. for 5 minutes at a rate of 7000 rpm by means of T.K. Homomixer ® (the same as above). Thereafter, 50 g of an aqueous solution containing 0.4 wt. % of Kelzan S ® (the same as above) and 0.8 wt. % of Veegum ® (the same as above) was added at room temperature and mixed for several minutes with mild stirring to obtain 100 g of a flowable formulation containing 10 wt. % of the active ingredient.

COMPARATIVE EXAMPLE 4

55 Grams of a 10 : 1 (by weight) mixture of the active ingredients (c) and (g) was added to 445 g of an aqueous solution containing 3 wt. % of Gosenol KH-17 ® (polyvinyl alcohol; a trade name of Nippon Gosei Kagaku Kogyo Co.; polymerization degree, 1500 or more; saponification degree, 78.5–81.5%) and 1 wt. % of Span 85 ® (sorbitan trioleate type dispersing agent; a trade name of Kao Co.). The resulting mixture was added to Dynomil KDL (a horizontal wet-pulverizer; produced by Willy A. Bachofen AG in Switzerland), and after adding glass beads of 1 mm in size, wet-pulverized at a rate of 3000 rpm until the size of the active ingredients in the mixture was 2 to 3 μm. Thereafter, 500 g of a 20 wt. % aqueous solution of Agrisol FL 100F ® (the same as above) previously neutralized was added and mixed for several minutes with mild stirring to obtain 1000 g of a flowable formulation containing 5.5 wt. % of the active ingredients.

TEST EXAMPLE 1

The oil-in-water emulsion formulations produced in Examples 1, 2 and 4 and the flowable formulations produced in Comparative Examples 1, 2 and 3 were each placed in a 100 ml polyethylene bottle, and after tightly stoppering, stored at 5° C. for 90 days. The formulations were then observed under a microscope (x 100) to find that crystals were formed in the formulation obtained in Comparative Examples, but that crystals were not formed at all in the formulation obtained in Examples.

TABLE 3

Results of crystallization-comparative test

| Test formulation | Crystallization | |
|---|---|---|
| | Immediately after production | After 5° C. × 90 days' storage |
| Example 1 | — | — |
| Comparative Example 1 | — | + |
| Example 2 | — | — |
| Comparative Example 2 | — | ++ |
| Example 4 | — | — |
| Comparative Example 3 | — | ++ |

Note:
−No crystals were formed.
+A trace amount of crystals was formed.
++A small amount of crystals was formed.

TEST EXAMPLE 2

The oil-in-water emulsion formulation produced in Example 7 and the flowable formulation produced in Comparative Example 4 were each placed in a 100 ml polyethylene bottole, and after tightly stoppering, stored for a period of 14 test cycles., 1 test cycle meaning a unit term of storage, −5° C.×4 days and then 30° C.×3 days. The formulations were then observed under a microscope (×100) to find that, with the formulation obtained in Comparative Example 4, the crystals grew and many of them settled down to the bottom f the polyethylene bottle, but that the formulation obtained in Example 7 kept an oil-in-water emulsion form with no formation of crystals.

TEST EXAMPLE 3

Phytotoxicity to Chinese cabbage (var., Muso) was tested using the oil-in-water emulsion formulation produced in Example 1 and the flowable formulation produced in Comparative Example 1.

Each formulation was applied in 250-fold dilute solution. The results are shown in Table 4 in an average phytotoxicity degree obtained from three replications per plot.

TABLE 4
Results of phytotoxicity-comparative test

| Test formulation | Average phytotoxicity degree |
|---|---|
| Example 1 | 0 |
| Comparative Example 1 | 0 |
| No treatment | 0 |

TEST EXAMPLE 4

A test on oral acute toxicity to rat was carried out using the oil-in-water emulsion formulation produced in Example 1.

As a result, the $LD_{50}$ value was 2,250 mg/kg for male and 2,150 mg/kg for female, the formulation being found to be very low in toxicity.

TEST EXAMPLE 5

Efficacy tests on pests were carried out using the oil-in-water emulsion formulation freshly produced in Example 1 and the flowable formulation produced in Comparative Example 1.

Each formulation was diluted to a prescribed concentration, and cabbage leaves of 5 cm x 5 cm in size were dipped in the diluted solution for 1 minutes. After drying, the leaves and 10 larvae of tobacco cutworm (*Spodoptera litura*) were placed in a cup of 9 cm in diameter. After 2 days, the mortality was examined (6 replications).

Separately, a small branch of peach on which mealy plum aphid (*Hyaloterus pruni*) were parasitic was inserted into a 200 ml Erlenmeyer flask, and the test formulation diluted to a prescribed concentration was sprayed onto it on a turn table. The number of mealy plum aphids on the peach branch was counted before spraying and one day after spraying, and the mortality was calculated (3 replications).

TABLE 5
Comparison of activity on tobacco cutworm

| Test formulation | $LC_{50}$ (ppm) |
|---|---|
| Example 1 | 20.9 |
| Comparative | 25.4 |

TABLE 5-continued
Comparison of activity on tobacco cutworm

| Test formulation | $LC_{50}$ (ppm) |
|---|---|
| Example 1 | |

TABLE 6
Comparison of activity on mealy plum aphid

| Test formulation | Mortality (%) Dilution rate | | |
|---|---|---|---|
| | 64000 | 16000 | 4000 |
| Example 1 | 54.5 | 67.9 | 88.4 |
| Comparative Example 1 | 43.6 | 68.9 | 66.8 |

What is claimed is:

1. An oil-in-water pesticidal emulsion which comprises one or more, of hydrocarbons represented by the formula,

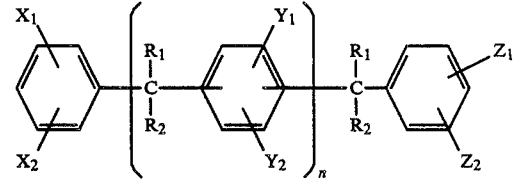

wherein $X_1$, $X_2$, $Y_1$, $Y_2$, $Z_1$ and $Z_2$, which may be the same or different, represent a hydrogen atom or an alkyl group having two or less carbon atoms, $R_1$ and $R_2$, which may be the same or different, represent a hydrogen atom or a methyl group, and n represents 0 or 1, in an oil-in-water pesticidal emulsion containing an active ingredient or mixture thereof having a pesticidal activity, wherein the melting point is 0° C. or higher and the solubility of the active ingredient or mixture thereof at 0° C. in the hydrocarbons represented by the above formula is 10 wt. % or more.

2. The oil-in-water pesticidal emulsion according to claim 1, wherein at least one of the active ingredients is a pyrethroid compound or its isomer.

3. The oil-in-water pesticidal emulsion according to claim 1 or 2, wherein at least one of the active ingredients is a pyrethroid compound or its isomer selected from the group consisting of:
α-cyano-3-phenoxybenzyl 3-(2,2-dichlorovinyl)-2,2-dimethylcyclopropanecarboxylate,
3-phenoxybenzyl 3-(2,2-dichlorovinyl)-2,2-dimethylcyclopropanecarboxylate,
α-cyano-3-phenoxybenzyl 2,2,3,3-tetramethylcyclopropanecarboxylate,
α-cyano-3-phenoxybenzyl 2-(4-chlorophenyl)-3-methylbutyrate, 3,4,5,6-tetrahydrophthalimidemethyl chrysanthemate and 3-phenoxybenzyl 2-(4-ethoxyphenyl)-2-methylpropyl ether.

4. The oil-in-water pesticidal emulsion according to claim 1, wherein at least one of the hydrocarbons is phenylxylylethane.

* * * * *